United States Patent [19]

Viscio

[11] Patent Number: 5,302,375
[45] Date of Patent: Apr. 12, 1994

[54] ORAL COMPOSITION HAVING IMPROVED TOOTH WHITENING EFFECT

[75] Inventor: David Viscio, Monmouth Jct., N.J.

[73] Assignee: Colgate-Palmolive Company, Piscataway, N.J.

[21] Appl. No.: 978,840

[22] Filed: Nov. 19, 1992

[51] Int. Cl.⁵ .................. A61K 7/16; A61K 7/20
[52] U.S. Cl. ................................ 424/53; 424/49
[58] Field of Search ........................ 424/49–58

[56] References Cited

U.S. PATENT DOCUMENTS

| | | | |
|---|---|---|---|
| 3,637,339 | 1/1972 | Gray | 8/111 |
| 4,079,016 | 3/1978 | Brahm et al. | 252/99 |
| 4,087,369 | 5/1978 | Wevers | 252/99 |
| 4,120,809 | 10/1978 | Murray | 252/102 |
| 4,421,668 | 12/1983 | Cox et al. | 252/174.12 |
| 4,886,615 | 12/1989 | Dehan | 252/90 |
| 5,004,556 | 4/1991 | Julemont et al. | 252/99 |
| 5,055,305 | 10/1991 | Young | 424/466 |
| 5,094,771 | 3/1992 | Ahmed et al. | 252/99 |
| 5,116,575 | 5/1992 | Badertscher et al. | 422/28 |
| 5,176,713 | 1/1993 | Dixit et al. | 8/137 |

FOREIGN PATENT DOCUMENTS 836988  6/1960  United Kingdom .

Primary Examiner—Shep K. Rose
Attorney, Agent, or Firm—Paul Shapiro; Robert C. Sullivan; Paul Shapiro

[57] ABSTRACT

The present invention provides an oral composition for whitening teeth comprising a safe and effective whitening amount of peracetic acid dissolved or suspended in a vehicle, wherein the peracetic acid is generated within the vehicle in situ by combining water, acetylsalicylic acid and a water soluble alkali metal percarbonate.

20 Claims, No Drawings

ORAL COMPOSITION HAVING IMPROVED TOOTH WHITENING EFFECT

BACKGROUND OF THE INVENTION

1. Field of the Invention

This invention relates generally to an oral composition which when applied onto the surface of teeth acts to whiten teeth and more particularly to an oral composition for whitening teeth that is more effective than existing products available to the consumer.

2. The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that an individual comes in contact with on a daily basis can "stain" or reduce the "whiteness" of one's teeth. In particular, foods, tobacco products and fluids such as tea and coffee that one consumes tend to stain the teeth. These products or substances tend to accumulate on the enamel layer of the tooth and form a pellicle film over the teeth. These staining and discoloring substances can then permeate the enamel layer.

One method for whitening teeth used by dental professionals involves the use of 30% hydrogen peroxide in combination with heat and light to promote the oxidation reaction. This method, although fast, is losing favor with dentists because clinical and scientific evidence shows that an effective whitening process without heat and light is desired.

Another professional method for bleaching teeth involves the use of hydrogen peroxide generating compounds such as urea peroxide (carbamide peroxide) at concentrations of 10% to achieve the desired whitening effect. Urea peroxide rapidly breaks down into hydrogen peroxide due to the water present in saliva. This method is known as an office-monitored at-home bleaching system and involves the use of a mouth guard or tray within which the bleaching agent is placed. The tray is then placed upon the teeth of the user and bleaching is allowed to take place. This method of treatment has drawbacks including tooth sensitivity, possibly due to demineralization and irritation of oral tissues. An additional disadvantage of the tray application method is that the bleaching effect is very slow.

There is a demand in the marketplace for a tooth whitening product that can be used at home or in private by the consumer and is safe and easy to use. A product for home use should not utilize the compositions or products for whitening teeth that are available for use by a trained dental professional. For example, the 30% hydrogen peroxide bleaching agent utilized by many dental practitioners to bleach teeth is sufficiently concentrated to be irritating and potentially dangerous for home use by the consumer.

More recently it has been discovered that peracetic acid is a surprisingly effective bleaching or whitening agent for discolored or stained human teeth, as disclosed in copending U.S. patent application Ser. No. 07/796,160, filed Nov. 22, 1991, the complete disclosure of which is incorporated herein by reference. As described in that application, 1% by weight aqueous solution of peracetic acid gives rise to a faster and superior whitening effect when applied to teeth at ambient to oral range temperatures than does a 30% by weight aqueous solution of hydrogen peroxide. As also described in the above referenced application, the peracetic acid can be applied directly to the teeth as by swab application, incorporated in an oral composition such as a toothpaste, gel or rinse that is to be applied topically, or generated in situ in the oral composition by the reaction of a peroxide source such as hydrogen peroxide, urea peroxide, sodium perborate, sodium percarbonate, and metal peroxides, for example, $SrO_2$, $CaO_2$ and $NaO_2$, with peroxyacid precursor or activator containing labile acetyl groups. Illustrative examples of such activators include tetracetylethylenediamine, pentaacetylglucose, tetracetylglycoluril, sorbitol hexaacetate or fructose pentaacetate.

One of the major disadvantages associated with the use of peracetic acid packaged for home use by the consumer is its relative instability. Dilute 1% aqueous solutions of peracetic acid will substantially decompose in as little as 30 days at ambient temperatures. Storage at 3° C. significantly improves stability but not to the extent required for the normal market age for a consumer or professional product. In addition, many common adjuvants present in consumer and professional products such as flavorants and other organic materials can rapidly react with peracetic acid, destroying both the adjuvants and the peracetic acid.

These factors tend to dictate that a preferred approach for the employment of peracetic acid chemistry in dentifrice applications is to generate the peracetic acid in-situ at the time of use. A source of hydrogen peroxide and a carboxylate derivative of acetic acid, such as an amide or an ester, may be mixed together in water at a pH high enough to generate sufficient concentration of perhydroxyl anion from the hydrogen peroxide. The perhydroxyl anion nucleophilically attacks the acetate derivative producing peracetic acid in accordance with the following reaction:

Analogous chemistry has been employed to generate hydrogen peroxide and perorganic acids in dry bleach and laundering compositions. For example, British Patent 836,988 discloses textile bleaching compositions containing an inorganic $H_2O_2$ source such as sodium perborate or sodium percarbonate and an organic carboxylic acid ester such as esters of phenols or esters of mono - or disaccharides containing 3 or more ester groups.

The in-situ approach towards generating peracetic acid has also been disclosed with respect to dentifrice compositions as described in U.S. patent application Ser. No. 07/796,160, referred to above.

In addition, U.S. Pat. No. 5,055,305 discloses effervescent tablets for the in vitro cleaning of dentures which contain, as essential components, a bleaching agent which comprises salts of persulfate perborate or pyrophosphate hydrates or metal peroxides, a peroxyacid bleach precursor and an effervescence—producing base composition. Among the numerous organic per-acid precursors disclosed are carboxylic acid esters such as acetylsalicylic acid, which are more generally disclosed in the aforementioned British Patent 836,988, directed towards textile bleaching and detergent compositions.

In those applications where dentifrice compositions are designed for in-vivo use, it is essential that the peracetic acid generating components react quickly after they are combined, since the user will normally wish to limit the time in which the dentifrice is in contact with the teeth. In addition, the classes of peroxide generators and peroxy acid bleach precursors useful for in-vivo application to the teeth is severely limited due to the requirement that these components by physiologically safe and non-irritating to oral tissues. A further requirement for in-vivo use is that the peracetic acid is generated at a relatively neutral pH, close to the safe physiological neutral pH of 7.

SUMMARY OF THE INVENTION

The present invention provides an oral composition for whitening teeth comprising a safe and effective whitening amount of peracetic acid dissolved or suspended in a vehicle, wherein the peracetic acid is generated within the vehicle in situ by combining water, acetylsalicylic acid and a water soluble alkali metal percarbonate.

The present invention offers the advantages that the peracetic acid is generated quickly and in large quantities and at a relatively low pH of less than about 9.0, thereby facilitating convenient and effective home use by the consumer as well as professional use by the dentist.

DETAILED DESCRIPTION OF THE INVENTION

The hydrogen peroxide source used in the compositions of the invention is a water soluble alkali metal percarbonate such as sodium or potassium percarbonate. The preferred hydrogen peroxide source is sodium percarbonate, also referred to as sodium carbonate peroxyhydrate, having the chemical formula $2Na_2CO_3 \cdot 3H_2O_2$. This material is particularly preferred because it is highly water soluble and dissolves quickly to react with acetylsalicylic acid to generate peracetic acid and also provides a source of alkalinity in the reaction medium.

The peracetic acid precursor used in combination with the percarbonate is acetylsalicylic acid (ortho-acetoxybenzoic acid), more commonly known as aspirin, and having the chemical formula $CH_3COOC_6H_4COOH$.

The percarbonate and acetylsalicylic acid components are each commercially available in fine powder form in both technical and pharmacological grades. When these components are dissolved in water at temperatures of 20° to 25° C., they quickly react to generate peracetic acid as a consequence of the nucleophilic attack by the perhydroxyl anion on the acetyl ester group of the acetylsalicylic acid. The presence of a carboxylic acid group on the acetylsalicylic acid molecule tends to neutralize some of the alkalinity generated as the result of the decomposition of the percarbonate, thereby resulting in a solution pH of less than 10, and generally in the range of from about 8.0 to about 9.0.

To enhance the performance of the peracetic acid as a whitening agent it is desirable to adjust the pH of the oral composition to the acid range, i.e. below pH 7.0 and preferably a pH of about 5.0 to about 6.5. To adjust the pH, any non-toxic acid or acid salt may be added to the oral composition. Preferably materials such as citric acid, tartaric acid, partial salts of these acids, monosodium hydrogen phosphate may be added to the oral compositions to obtain an acid pH.

The amount of peracetic acid incorporated in the oral compositions may vary depending upon intended use. For use by trained professionals in office treatments, the concentration of peracetic acid may range from about 0.25 to 5% by weight. For home use, lower concentrations of peracetic acid are dictated, generally in the range of from about 0.01 to about 0.50% by weight. Translating these values into the content of peracetic acid precursors required to generate such quantities of peracetic acid, the oral compositions may contain from about 0.5 to about 35% by weight of the combination of alkali metal percarbonate and acetylsalicylic acid incorporated therein, more preferably from about 1 to about 20% by weight. The preferred weight ratio of alkali metal percarbonate to acetylsalicylic acid may range from about 4:1 to 1:4. The more preferred weight ratio of sodium percarbonate to acetylsalicylic acid lies in the range of from about 1:1 to about 2:1, most preferably about 1.6:1.

The vehicle used for preparing the oral compositions of the present invention may include water, water-containing oral rinses, pastes, gels and similar forms as are known in the art. For professional or home use, measured quantities of the percarbonate and acetylsalicylic acid can be individually dissolved in water and permitted to react to form a solution having the desired concentration of peracetic acid, e.g., a concentration of from about 0.1 to about 5% by weight. For professional use, this solution can additionally be gelled using fumed silica or a nonionic gellant such as hydroxyethylcellulose, and applied to the patient's teeth by the dentist. A particularly preferred adaptation is the provision of a dry powdered mixture of these components or a multilayer tablet wherein one layer contains the peracarbonate component and a different layer contains the acetylsalicylic acid component.

Where the oral composition is in the form of a paste or gel wherein the vehicle already contains some water, such as a tooth paste, quite clearly the reactive components must be separated to avoid chemical reaction prior to use by the consumer. Such an oral composition can be provided in the form of at least two separate, unmixed carrier phases, including a non-aqueous phase containing the percarbonate and an aqueous phase containing the acetylsalicylic acid. Such separation can also be provided by encapsulating one or both components in a material which will dissolve in water or fracture when the composition is used by the consumer.

Gels or pastes formulated to contain the acetylsalicyclic acid ingredient of this invention may also include a gelling agent such as a polyoxyethylene-polyoxypropylene block copolymer, a humectant such as glycerine, sorbitol or a polyethylene glycol, a nonionic surfactant, sweetener and flavorant. Water may be present in the gel or paste and generally constitutes about 40–70% by weight of the oral composition. Distilled or deionized water is preferred to prevent minimal contamination.

Polyoxyethylene-polyoxypropylene block copolymers which are nonionic and useful gelling agents in the oral compositions of the present invention are represented by the formula:

$$HO(C_2H_4O)_b(C_3H_6O)_a(C_2H_4O)_bH$$

wherein a is an integer such that the hydrophobic base represented by $(C_3H_4O)$ has a molecular weight of about 2750 to 4000, b is an integer such that the hydrophilic portion (moiety) represented by $(C_2H_4O)$ constitutes about 70–80% by weight of the copolymer. Pluronic TM Polyols of the F (solid flake or powder) type are preferred.

Other useful thickening agents include colloidal carboxyvinyl polymers, cross-linked polycarboxylate polymers, polyvinyl pyrrolidone, and fumed silica.

The gelling agent may be present in the oral composition of the present invention at a concentration of about 0.25 to about 40% by weight and preferably about 0.5 to about 30% by weight of the composition.

Illustrative of the polyethylene glycols useful as additives include polyethylene glycols known by the trademark CARBOWAX TM which are nonionic polymers of ethylene oxide having the general formula:

$$HOCH_2(CH_2CH_2O)_nCH_2OH$$

wherein n represents the average number of oxyethylene groups. The Carbowax TM polyethylene glycols are designated by a number such as 400, 600, 800, etc. which represents the average molecular weight. The average molecular weight of the polyethylene glycols used herein is about 200–1000, preferably 400–800 and most preferably 600.

Other useful humectants include non-hydroxylated compositions such as capped polyethylene glycol, where the hydrogens on the hydroxyl groups have been replaced with methyl groups. Humectants such as glycerine, sorbitol polyethylene glycol and capped polyethylene glycols may be included in the oral composition of the present invention at a concentration of about 10 to about 40% by weight and preferably about 15 to about 25% by weight of the composition.

Surfactants such as anionic and nonionic compounds may be included in the oral compositions of the present invention to serve as a wetting, solubilizing and emulsifying agents. Particularly useful anionic surfactants include sodium lauryl sulfate, salts of dodecylbenzene sulfonate and sodium coconut monoglyceride sulfonates. A particularly useful nonionic surfactant is a water soluble polyoxyethylene monoester of sorbitol with a $C_{10-18}$ fatty acid ester of sorbitol (and sorbitol anhydrides), consisting predominantly of the monoester, condensed with about 10–30, preferably about 20, moles of ethyleneoxide. The fatty acid (aliphatic hydrocarbon-monocarboxylic acid) may be saturated or unsaturated, e.g. lauric, palmitic, stearic or oleic acids. Tween TM 20 is especially preferred, which is a polyoxyethylene (20) sorbitan monolaurate. Capped polyalkylene oxide copolymer nonionic surfactants in which the hydrogens on the hydroxyl groups have been replaced with methyl groups are also useful in the present invention. These types of surfactants are described in U.S. Pat. Nos. 4,988,452 and 4,877,544.

The surfactant constitutes about 0.1 to 5.0% by weight and preferably 0.5 to 3% by weight of the oral composition.

A flavor ingredient may constitute about 0.5 to 5.0% by weight of the oral composition of the present invention. Suitable flavoring constituents are flavoring oils, e.g., oils of spearmint, peppermint, wintergreen, sassafras, clove, sage, eucalyptus, marjoram, cinnamon, and methyl salicylate, ethyl acetate and menthol.

A sweetening material is preferably also employed as a complement to the flavoring material. Suitable sweetening agents are water soluble and include sodium saccharin, sodium cyclamate, xylitol, aspartame and the like, in concentrations of about 0.10 to 1.0% by weight. Sodium saccharin is preferred.

Pyrophosphate salts having anti-tartar efficacy such as a dialkali or tetra-alkali metal pyrophosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphates such as sodium trimetaphosphate may also be incorporated in the oral compositions of the present invention preferably at a concentration of about 0.5 to about 8.0% by weight.

Peroxide stabilizers such as sequestering agents, buffers, acidulating agents, coating or encapsulating agents may also be included in the oral compositions of the present invention. Examples of suitable sequestering agents are salts of ethylenediaminetetraacetic acid, diethylene triaminepentaacetic acid, phosphonates such as DEQUEST available from Monsanto Chemical Company and azacycloheptane 2',2' diphosphonate. Such agents stabilize the peroxide containing compositions by chelating metal ions such as $Fe^{+3}$, $Mn^{+2}$ and $Cu^{+2}$. The agents may be incorporated in the compositions of the present invention at a concentration of about 0.1 to about 6.0% by weight of the composition.

The composition of the invention may also be formulated into an effervescent tablet composition for use in cleaning dentures. In this embodiment the tablet would be composed of an acidic layer containing the acetylsalicylic acid component and an effervescent such as sodium bicarbonate, and an alkaline layer containing the alkali metal percarbonate. Tablets of this type are disclosed in U.S. Pat. No. 5,055,305.

The following Example 1 illustrates the enhanced whitening effect on human teeth of a 1% by weight aqueous peracetic acid solution as compared with a 30% by weight aqueous solution of hydrogen peroxide.

EXAMPLE I

A Minolta CR-221 Chroma Meter was used to measure the optical properties of extracted human molars and after application of whitening agents.

The whitening agents tested were:
1. The System—5.5 grams of sodium percarbonate and 2.5 grams of aspirin were dissolved in 100 mL of water. After reacting for 2–3 minutes, 3.7 grams of citric acid were added to give a solution with a final pH of about 6.
2. 1% Peracetic acid—A solution of 1% peracetic acid in water was made and pH adjusted to about 4 with sodium hydroxide.
3. 30% Hydrogen peroxide—30% hydrogen peroxide was used as obtained from the bottle.
4. 3% Hydrogen peroxide—30% hydrogen peroxide was diluted in water to 3% and a pH of 4.9

The Minolta Chroma Meter has a 3 mm diameter circular aperture for measuring optical properties of small areas. The meter provides values of the optical parameters L* and b* in the CIE system of color measurement. L* relates to the overall grey scale lightness or darkness of the material and b* relates to the yellowness or blueness. Other factors being equal, it is preferred to have high values of L*, indicating lightness, and low or even negative values of b*, indicating absence of yellowness. Since no two teeth have identical optical properties, the whitening performance of various agents is tested by monitoring the change in L* and b* (dL* and db*) as a function of time and treatment.

The teeth to be bleached had been stored under refrigeration in water since extraction. Each tooth was suspended in 25 mL of the whitening solutions at room temperature. Two teeth were used per treatment and two spots on each tooth was measured. At regular time intervals the teeth were removed from the solutions for optical measurements then replaced back into the solutions. The results as average dL* and db* are shown in Table 1.

TABLE 1

| | dL*/db* | | | |
|---|---|---|---|---|
| | Time (min) | | | |
| | 15 | 30 | 45 | 60 |
| System | 2.16/−2.79 | 3.12/−4.18 | 3.19/−3.37 | 3.11/−3.85 |
| 1% PAA | 2.73/−2.16 | 2.37/−3.07 | 3.87/−3.34 | 4.09/−3.19 |
| 30% $H_2O_2$ | 0.69/−1.37 | 1.30/−2.03 | 1.69/−2.77 | 2.30/−3.13 |
| 3% $H_2O_2$ | 0.66/−0.40 | 0.02/−0.50 | 0.75/−1.65 | 1.43/−2.04 |

These results clearly show the superiority of peracetic acid for whitening teeth and that a system for in-situ generation of peracetic acid can deliver similar performance.

Example 2 illustrates the in-situ preparation of peracetic acid from a mixture of sodium percarbonate and acetylsalicylic acid. EXAMPLE 2

5.5 grams of sodium percarbonate and 2.5 grams of acetylsalicylic acid were dissolved in 100 mL of water at room temperature. The amount of percarbonate and acid employed was calculated to deliver a theoretical maximum peracetic acid level of 1.0%. At regular time intervals, 3 mL aliquots of the solution were withdrawn and the concentration of peracetic acid (PA) was measured by standard iodometric titration.

pH measurements were also recorded as a function of time. The rate and concentration of peracetic acid formation and solution pH are recorded in Table 2.

The following comparative examples illustrates the rapidity of peracetic acid generation of the composition of the present invention as compared with a combination of sodium percarbonate and other known peracetic acid precursors, glucose pentaacetate (GPA) and tetraacetylethylenediamine (TAED).

COMPARATIVE EXAMPLE 3

5.5 grams of sodium percarbonate and 1.2 grams of GPA were dissolved in 100 mL of water at room temperature. The level of GPA was selected to also deliver the theoretical maximum peracetic acid level of 1.0%, as in Example 2. 3 mL aliquots of this solution were taken at regular time intervals, and peracetic acid concentration and pH were measured as in Example 2. Results are recorded in Table 2.

COMPARATIVE EXAMPLE 4

5.5 grams of sodium percarbonate and 1.5 grams of tetraacetylethylenediamine (TAED), another known peracetic acid precursor, were dissolved in 100 mL of water at room temperature. The level of TAED was selected to deliver the theoretical maximum peracetic acid level of 1.0%, as in Examples 2 and 3. Three (3) mL aliquots of this solution were taken at regular time intervals, and the peracetic acid concentration and pH were measured as in Examples 1 and 2. The results are shown in Table 2.

TABLE 2

| | Time (min) | | | | | | | |
|---|---|---|---|---|---|---|---|---|
| | 0 | 0.5 | 1.0 | 2.0 | 5.0 | 10.0 | 20.0 | 40.0 |
| Ex 2 (Aspirin) | | | | | | | | |
| PAA conc (%) | 0 | 0.64 | 0.88 | 1.01 | 1.02 | 1.01 | 0.97 | 0.91 |
| pH | 9.3 | — | 8.8 | 8.9 | 8.8 | 8.8 | 8.8 | 8.8 |
| Ex 3 (GPA) | | | | | | | | |
| PAA conc (%) | 0 | 0.21 | 0.35 | 0.61 | 0.84 | 0.99 | 1.04 | 1.04 |
| pH | 10.6 | — | 10.2 | 10.1 | 9.9 | 9.8 | 9.8 | 9.8 |
| Ex 4 (TAED) | | | | | | | | |
| PAA conc (%) | 0 | 0.04 | 0.27 | 0.51 | 0.85 | 0.98 | 1.01 | 0.97 |
| pH | 10.4 | — | 10.1 | 10.0 | 9.8 | 9.8 | 9.8 | 9.8 |

As is evident from Table 2, the composition containing acetylsalicylic acid (aspirin) generated about 100% (1.0%) of the theoretical maximum peracetic acid within two minutes and provided a solution having a relatively mild pH of about 8.8. In contrast, the composition containing GPA and TAED delivered only about 61% and 51% respectively of the theoretical maximum peracetic acid over the same two minute time period and required a total of about ten minutes to achieve the same concentration of 1.0% as achieved by the acetylsalicylic acid-containing composition in two minutes.

In addition, the comparative pH measurements demonstrate that the composition containing acetylsalicylic acid yielded a pH consistently about one unit lower than the comparable composition containing GPA or TED.

The present invention thus provides oral compositions which generate peracetic acid quickly and effectively for application to the teeth while at the same time generating pH values in said compositions more nearly approaching the safer physiological neutral pH of 7.

EXAMPLE 5

A sodium percarbonate gel composition was prepared by dispersing 0.5 grams of Carbopol TM 941 in 100 grams of glycerin. Thereafter 11 grams of sodium percarbonate were dispersed into the glycerin gel.

A stock gel was prepared by dispersing 12 grams of hydroxyethylcellulose in 388 grams of water. Three separate activator gels were made by adding 5 grams of aspirin, 2.4 grams of GPA, or 3 grams of TAED to 100 grams of the stock gel.

5 grams of each activator gel were mixed with 5 grams of the sodium percarbonate gel. After ten minutes, peracetic acid concentration in each gel was measured.

TABLE 3

| Activator | PAA conc |
|---|---|
| Aspirin | 0.62% |
| GPA | 0.38% |
| TAED | 0.40% |

The data in Table 3 demonstrate the superiority of aspirin in generating PAA in gel compositions of the type used in oral care compositions when compared to bleach activators such as GPA and TAED commonly used to enhance the performance of hydrogen peroxide bleaching systems.

What is claimed is:

1. A tooth whitening composition for whitening teeth in the oral cavity comprising a safe and effective tooth whitening amount of peracetic acid wherein there is provided separate unmixed phases comprised of (a) a water soluble alkali metal carbonate contained in a non-aqueous carrier and unmixed (b) acetyl salicylic acid in a weight ratio of (a):(b) of 4:1:1:4, the two phases being combined shortly before application to the teeth in the presence of water, the pH of the combined phases being at a pH of 7 or below whereby said peracetic acid is generated in situ and is effective for whitening teeth when allowed to remain on the teeth for a time sufficient to effect whitening thereof.

2. The composition of claim 1 wherein said alkali metal percarbonate is sodium percarbonate.

3. The composition of claim 1 wherein said peracetic acid is present in said composition at a concentration of from about 0.01 to about 5.0% by weight.

4. The composition of claim 3 wherein said acetylsalicylic acid and percarbonate are present in said composition in a weight ratio of from about 4:1 to 1:4 respectively.

5. The oral composition of claim 1 wherein said vehicle is a gel.

6. An oral composition for whitening teeth containing acetylsalicylic acid and an alkali metal percarbonate.

7. The composition of claim 6 wherein said acetylsalicylic acid and said percarbonate are present in said composition at a combined concentration of from about 0.5 to about 35% by weight.

8. The composition of claim 7 wherein said acetylsalicylic acid and percarbonate are present in said composition in a respective weight ratio of from about 4:1 to about 1:4.

9. The composition of claim 8 wherein said percarbonate is sodium percarbonate.

10. The composition of claim 6 wherein said acetylsalicylic acid and said alkali metal percarbonate are present in discrete particulate form.

11. The composition of claim 6 wherein said composition is in the form of at least two separate, unmixed carrier phases, one phase containing said acetylsalicylic acid and a different phase containing said alkali metal percarbonate.

12. The composition of claim 1 wherein the pH is below 7.0.

13. The composition of claim 1 wherein the pH is about 5.0 to about 6.5.

14. A method for whitening teeth in the oral cavity comprising preparing two separate unmixed phases comprised of (a) a water soluble metal percarbonate contained in a non-aqueous carrier and unmixed (b) acetylsalicylic acid, in a weight ratio of (a):(b) of 4:1 to 1:4. and then shortly before application to the teeth to be whitened in the oral cavity combining water and (a) and (b) to generate a whitening amount of peracetic acid in situ at a pH of 7 or below, applying the combination to the teeth in the oral cavity and then maintaining the combination in contact with the teeth for a time sufficient to effectively whiten the teeth.

15. A method for whitening teeth comprising applying to the teeth in the oral cavity the composition of claim 5.

16. A method for whitening teeth comprising applying to the teeth in the oral cavity the composition of claim 6 mixed with water.

17. The method of claim 14 wherein said alkali metal percarbonate is sodium percarbonate.

18. The method of claim 14 wherein the peracetic acid is present in the composition at a concentration of from about 0.01 to about 5.0% by weight.

19. The method of claim 14 wherein the acetylsalicylic acid and the alkali metal percarbonate are present in discrete particulate form.

20. The method of claim 14 wherein the pH of the composition is about 5.0 to about 6.5.

* * * * *